United States Patent
Suzuki et al.

(10) Patent No.: US 8,537,211 B2
(45) Date of Patent: Sep. 17, 2013

(54) IMAGE MANAGING APPARATUS

(71) Applicant: Olympus Medical Systems Corp., Tokyo (JP)

(72) Inventors: Koji Suzuki, Tokyo (JP); Koichi Hirose, Tokyo (JP); Hirofumi Inaba, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/626,134

(22) Filed: Sep. 25, 2012

(65) Prior Publication Data

US 2013/0100265 A1    Apr. 25, 2013

Related U.S. Application Data

(63) Continuation of application No. PCT/JP2012/001331, filed on Feb. 27, 2012.

(30) Foreign Application Priority Data

Mar. 25, 2011 (JP) ................................. 2011-068753

(51) Int. Cl.
*H04N 9/47* (2006.01)
*H04N 7/18* (2006.01)

(52) U.S. Cl.
USPC .................. 348/74; 348/61; 348/65; 348/72; 348/76

(58) Field of Classification Search
USPC .................... 348/61, 65, 72, 74, 76
See application file for complete search history.

(56) References Cited

U.S. PATENT DOCUMENTS

| | | | |
|---|---|---|---|
| 6,349,373 B2* | 2/2002 | Sitka et al. | 711/161 |
| 6,574,629 B1* | 6/2003 | Cooke et al. | 1/1 |
| 7,092,970 B2* | 8/2006 | Shiibashi et al. | 1/1 |

(Continued)

FOREIGN PATENT DOCUMENTS

| | | |
|---|---|---|
| EP | 1 982 638 A1 | 10/2008 |
| EP | 2 140 800 A1 | 1/2010 |

(Continued)

OTHER PUBLICATIONS

International Search Report PCT/JP2012/001331 dated May 29, 2012 together with an English language translation.

(Continued)

*Primary Examiner* — Sath V Perungavoor
*Assistant Examiner* — Geepy Pe
(74) *Attorney, Agent, or Firm* — Scully, Scott, Murphy & Presser, P.C.

(57) ABSTRACT

In an image managing apparatus connected to: an image processing apparatus receiving an image signal from an imaging apparatus capturing a medical examination image; and an image recording apparatus recording a captured image, an apparatus information storage stores an image processing apparatus type. An apparatus ID acquiring unit acquires an image processing apparatus identifier from the connected image processing apparatus. An apparatus type acquiring unit reads out the type of the connected image processing apparatus based on the image processing apparatus identifier acquired by the apparatus ID acquiring unit. If the image processing apparatus type read by the apparatus type acquiring unit indicates that the apparatus can transmit an image file directly to the image recording apparatus, a file acquiring unit reads out from the image recording apparatus an image file that the image processing apparatus stores directly in the image recording apparatus.

7 Claims, 6 Drawing Sheets

(56) References Cited

U.S. PATENT DOCUMENTS

| | | | |
|---|---|---|---|
| 7,787,672 B2* | 8/2010 | Reicher et al. | 382/128 |
| 7,970,625 B2* | 6/2011 | Reicher et al. | 705/2 |
| 2002/0071101 A1* | 6/2002 | Horbaschek et al. | 353/28 |
| 2002/0081039 A1 | 6/2002 | Funahashi | |
| 2006/0095429 A1* | 5/2006 | Abhyankar et al. | 707/7 |
| 2007/0287900 A1* | 12/2007 | Breen et al. | 600/407 |
| 2009/0202123 A1 | 8/2009 | Pan | |

FOREIGN PATENT DOCUMENTS

| | | |
|---|---|---|
| JP | 2001-97414 | 4/2001 |
| JP | 2001-101320 | 4/2001 |
| JP | 2002-111987 | 4/2002 |
| JP | 2003-233674 | 8/2003 |
| JP | 2004-337503 | 12/2004 |
| JP | 2006-175215 | 7/2006 |
| JP | 2006-334322 | 12/2006 |
| JP | 2008-228898 | 10/2008 |

OTHER PUBLICATIONS

European Search Report dated Jul. 23, 2013 from corresponding European Patent Application No. 12 76 4438.3.

* cited by examiner

FIG.2

| APPARATUS IDENTIFIER 302 | APPARATUS TYPE 304 | CONNECTION STATUS 306 |
|---|---|---|
| ABC-01 | CAN NOT SEND FILE DIRECTLY | NOT CONNECTED |
| ABC-02 | CAN SEND FILE DIRECTLY | BEING CONNECTED |
| DEF-02 | CAN NOT SEND FILE DIRECTLY | NOT CONNECTED |
| DEF-03 | CAN SEND FILE DIRECTLY | NOT CONNECTED |

300

IMAGE MANAGING APPARATUS

CROSS-REFERENCE TO RELATED APPLICATIONS

This application is a continuation of and claims priority to PCT/JP2012/001331 filed Feb. 27, 2012, which claims the benefit of and priority from Japanese Patent Application No. 2011-68753 filed Mar. 25, 2011, the entire contents of these applications are incorporated herein by reference.

BACKGROUND OF THE INVENTION

1. Field of the Invention

The present invention generally relates to image processing technology, and more particularly, to an image managing apparatus for processing images captured by medical examination devices.

2. Description of the Related Art

According to prior arts, images captured by medical examination devices are recorded on photographic plates, photographic films, prints, or the like. Nowadays, an examination device on which an imaging device such as a CCD is mounted, and a computer have become widely available. As a result, these days, medical examination images are typically recorded as data in a recording apparatus or the like, electronically.

For example, patent document 1 shows a medical image system. In this medical image system, medical image data generated by a modality is usually sent to an image testing apparatus. The image testing apparatus checks an image, and medical image data of which the image is checked is stored and managed by an image storing communication system. On the other hand, in case that the image testing apparatus can not check an image because of failure or the like, medical image data is transmitted directly to the image storing communication system and the medical image data is stored without being checked.

Patent document 2 shows an endoscope system. In this endoscope system, an endoscope that outputs a captured image of a subject as an image signal, and a still image storing apparatus, such as a printer or the like, are connected via a processor. The processor performs signal processing on the image signal output by the endoscope, and outputs as video signals to the still image storing apparatus, such as a printer or the like. For example, in case of detecting that the printer is busy, the processor controls the system so that video signals on which the signal processing is performed is output to an image data storing apparatus, such as a PC card, or the like.

Patent document 3 shows an endoscope system that is used in industrial fields, for example for aircraft engine maintenance, for maintenance of piping system in a huge plant, or the like. In this endoscope system, an image is captured by an endoscope apparatus at each examination site, and the captured image is directly transmitted by email to a captured image managing computer in a control center, which is set as a distribution target. The captured image managing computer in the control center receives captured images transmitted from respective endoscope apparatuses by email and manages the images, in a concentrated manner.

[Patent Document No. 1] Japanese Patent Application Publication No. 2008-228898

[Patent Document No. 2] Japanese Patent Application Publication No. 2006-334322

[Patent Document No. 3] Japanese Patent Application Publication No. 2006-175215

Along with the development of medical examination devices, an imaging apparatus, an image processing apparatus, or the like, which are downsized, with enhanced performance, and/or with higher functionalities, have been released one after another. Also in medical institutions such as a hospital or the like, there is naturally a demand for introduction of latest medical examination devices. However, state-of-the-art medical examination devices are relatively expensive. Thus, even if a latest device is released, it is difficult to replace all the medical examination devices by purchasing the latest devices at once due to budget limitations. Therefore, in most medical institutions, medical examinations are carried out in an environment where different types of or different generations of imaging apparatuses, image processing apparatuses, or the like coexist.

In such situations, even in case of carrying out same type of examinations, procedure details (e.g., a method for recording image data) may be different depending on different types of or different generations of imaging apparatuses, image processing apparatuses, or the like. This increases the number of things for users (e.g., a doctor, a medical technologist, or the like) to remember. Therefore, in examinations using an imaging apparatus, an image processing apparatus, or the like, it is required to operate those apparatuses effectively.

SUMMARY OF THE INVENTION

According to an exemplary embodiment, an image managing apparatus is provided. The image managing apparatus is configured to be connected to an image processing apparatus that receives image signals from an imaging apparatus that captures a medical examination image, and to be connected to an image recording apparatus that records a captured image. The image managing apparatus includes: an apparatus information storage operative to store an image processing apparatus identifier and an image processing apparatus type, which indicates whether or not the image processing apparatus can transmit an image file directly to the image recording apparatus, while associating the identifier and the type with each other for more than one image processing apparatuses; an apparatus ID acquiring unit operative to acquire an image processing apparatus identifier from the connected image processing apparatus; an apparatus type acquiring unit operative to refer to the apparatus information storage on the basis of the image processing apparatus identifier acquired by the apparatus ID acquiring unit and operative to read out the type of the connected image processing apparatus; an image file acquiring unit operative, if the image processing apparatus type read by the apparatus type acquiring unit indicates that the image processing apparatus can transmit an image file directly to the image recording apparatus, to read out from the image recording apparatus an image file that the image processing apparatus stores directly in the image recording apparatus; an image file generating unit operative, if the image processing apparatus type read by the apparatus type acquiring unit indicates that the image processing apparatus can not transmit an image file directly to the image recording apparatus, to process a video signal transmitted from the image processing apparatus and to generate an image file; an image file transfer unit operative to transfer the image file generated by the image file generating unit to the image recording apparatus in order to allow the image recording apparatus to store the image file; and a screen image generating unit operative to generate a screen image for displaying the image file generated by the image file generating unit or the image file acquired by the image file acquiring unit on a display.

BRIEF DESCRIPTION OF THE DRAWINGS

FIG. 2 shows an example of an apparatus information table stored in an apparatus information storage in the image managing apparatus according to the exemplary embodiment;

DETAILED DESCRIPTION OF THE INVENTION

Figure 1:
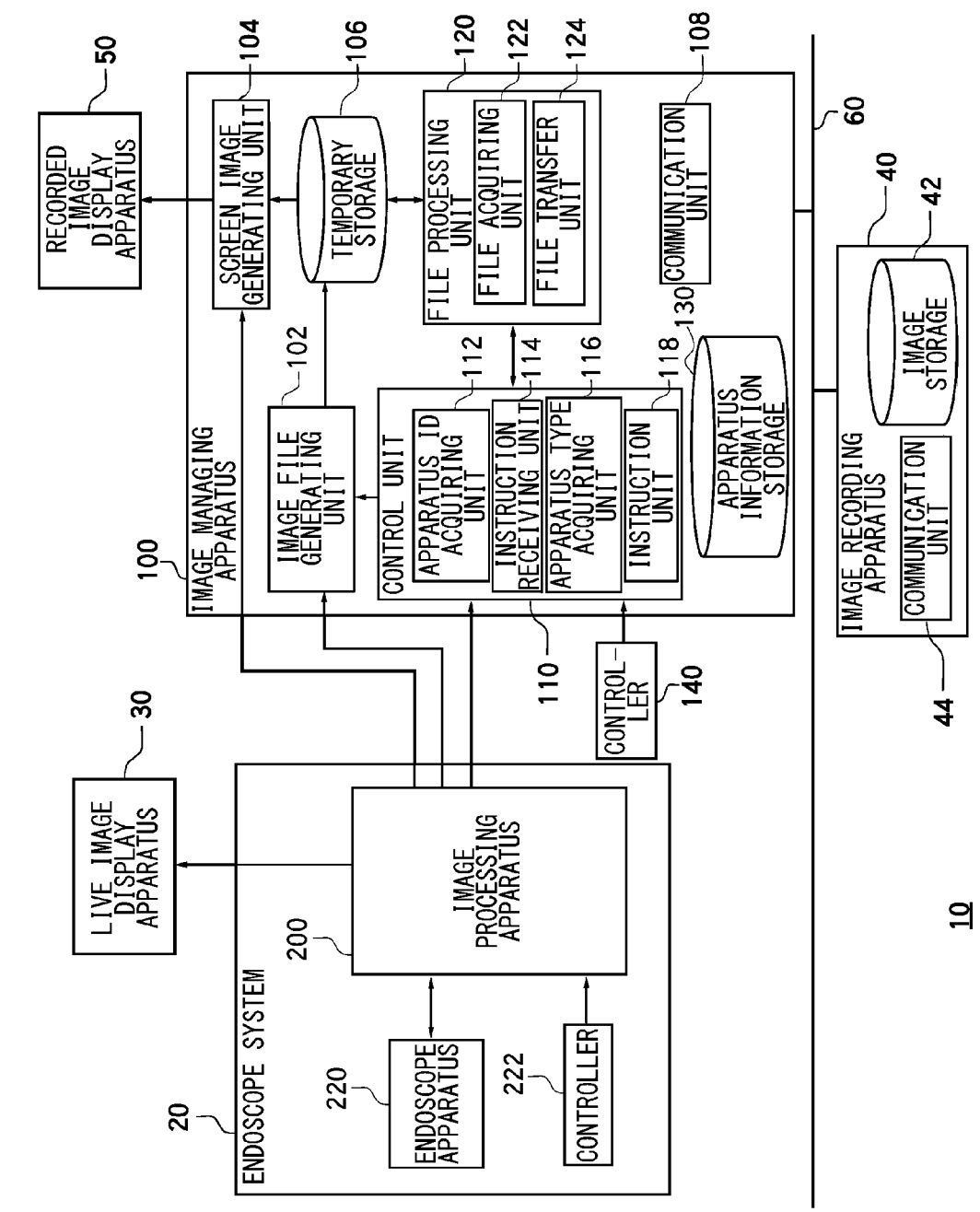
FIG. 1 shows a configuration of a medical examination support system including an image managing apparatus according to an exemplary embodiment.

The invention will now be described by reference to the preferred embodiments. This does not intend to limit the scope of the present invention, but to exemplify the invention.

First, a general description will be given on an exemplary embodiment. During a medical examination where an area to be examined is larger than an imaging area of an imaging apparatus by a single capture of a still image (for example, in case of an endoscopic examination, an ultrasonic examination, or the like), a doctor, a medical technologist, or the like carry out the examination by gradually moving an endoscope, a probe, or the like while monitoring a live image captured by a camera, a probe, or the like. At a region where an abnormality is found, or a region that is specified by an inspection order or the like in advance, a still image and/or a moving image are stored as a record of the medical examination. In this process, a user displays each of the recorded images on the spot and checks whether or not the images are taken appropriately. If necessary, the user takes an image of the region once again.

Therefore, in a system that performs such examinations, it is necessary during an examination to display an image being captured by a camera or the like as a live image, and to display on the spot an image stored in a recording apparatus as an examination record.

An image signal output from an imaging apparatus, such as an endoscope, an ultrasound probe, or the like, is input to an image processing apparatus. The image processing apparatus processes the image signal output from the imaging apparatus and converts the signal to a video signal, i.e. to a format that can be displayed on a monitor or the like as a live image.

Some image processing apparatuses can further convert the image signal output from the imaging apparatus to an image file format for storing in a recording apparatus, and can transfer the image file to a recording apparatus via a network so as to directly allow the recording apparatus to store the image file.

On the other hand, some image processing apparatuses do not have a function to generate and transfer an image file. In case of using such an image processing apparatus, it is necessary to set an intervening apparatus, which has a function to convert video signal to an image file format for storing in a recording apparatus, between the image processing apparatus and a recording apparatus.

An image managing apparatus according to an exemplary embodiment is connected between an image processing apparatus and a recording apparatus. The image managing apparatus can read the identifier of the image processing apparatus and determine the type of the image processing apparatus, and can allow the recording apparatus to store an image file by using different routes depending on the type of the image processing apparatus. Further, the image managing apparatus according to the exemplary embodiment can automatically display the stored image file on a monitor for checking recorded images even in case that an apparatus that generates an image file and/or a route for transferring an image file differ depending on the type of the image processing apparatus. This allows a user to issue an instruction for capturing an image, and to check a captured image without concern for a difference in the types of image processing apparatuses. Therefore, this relieves users (e.g., a doctor, a medical technologist, or the like) from spending time on tasks that have nothing to do with their essential job functions. Further, a situation where time to spend on an examination and/or observation is prolonged can be avoided.

By referring to figures, an explanation will be given below on the configuration of an image managing apparatus 100 according to an exemplary embodiment of the present invention.

FIG. 1 shows a configuration of a medical examination support system 10 including the image managing apparatus 100 according to the exemplary embodiment. The medical examination support system 10 is a system for supporting examination service including image capturing performed in a medical facility, such as a hospital or the like. In the exemplary embodiment, an example of medical examination support system 10 is shown that includes an endoscope apparatus, which is an example of an imaging apparatus for capturing a medical examination image.

The medical examination support system 10 comprises an endoscope system 20, an image managing apparatus 100, and an image recording apparatus 40 that records, as an image file, image data of an examination image captured by the endoscope system 20. Although only one pair of the endoscope system 20 and the image managing apparatus 100 is shown in FIG. 1, a plurality of endoscope systems 20 and/or image managing apparatuses 100 may be provided. For example, an endoscope system 20 and an image managing apparatus 100 may be provided in each of a plurality of examination rooms in a medical facility.

The image managing apparatus 100 and the image recording apparatus 40 are communicably connected via a network 60, such as, an intranet, a local area network (LAN), a wide area network (WAN), a virtual private network (VPN), the Internet, or the like. As will be described later, some of the endoscope systems 20 are of a type that is connected to the network 60, and some of the endoscope systems 20 are of a type that is not connected to the network 60.

The endoscope system 20 and the image managing apparatus 100 are directly connected to each other by a cable or the like. The endoscope system 20 and the image managing apparatus 100 may be connected by a plurality of cables, for example by two cables, one is for transmitting video signals from the endoscope system 20 to the image managing apparatus 100, and the other is for sending and receiving control signals to and from each other.

The endoscope system 20 comprises an endoscope apparatus 220, a controller 222, and an image processing apparatus 200, and is connected to a live image display apparatus 30. The endoscope apparatus 220 is inserted into the body of an examinee, captures an image of the inside of the body by a solid image pickup device (e.g., a CCD or the like) on the tip thereof, and outputs the captured image as an image signal to the image processing apparatus 200.

The controller 222 comprises a pointing device (e.g., a switch, a keyboard, a mouth, a trackball, or the like), a touch panel, a microphone, etc. The controller 222 is used for allowing a user to input an instruction (e.g., an instruction to start capturing an image, to stop capturing an image, to specify a condition for capturing image, etc.) to the image processing apparatus 200. The controller 222 may be formed integrally with the endoscope apparatus 220. A plurality of controllers 222 may be provided. The live image display apparatus 30 receives a video signal, which the image processing apparatus 200 outputs by processing a signal of an image captured by the endoscope apparatus 220. The live image display apparatus 30 displays the received video signal as a live image.

The image processing apparatus 200 outputs a drive control signal for controlling the endoscope apparatus 220 to the endoscope apparatus 220. The image processing apparatus 200 processes an image signal input from the endoscope apparatus 220. For example, the image processing apparatus 200 performs amplification, elimination of noise data, an analog digital conversion, a gain adjustment, an adjustment of luminance ratio, filtering, etc., so as to generate a video signal for displaying on a monitor an image captured by the solid image pickup device as a live image, i.e., so as to generate a screen image.

Some of the image processing apparatuses 200 are of a type that has, in addition to the functions described above, a function to generate an image file by itself and to transfer the image file to the image recording apparatus 40 via a network so as to allow the image recording apparatus 40 to store the image file. On the other hand, some of the image processing apparatuses are of a type that cannot generate an image file by itself and cannot transfer an image file via a network. In case that an image processing apparatus 200 does not have a network communication function, the image processing apparatus 200 will not be connected to the network 60. In this description, these different types of image processing apparatuses are collectively referred to as "image processing apparatuses 200".

The image recording apparatus 40 comprises an image storage 42, and a communication unit 44. The image storage 42 stores as an image file a photograph, a moving image, or the like, which the endoscope system 20 has captured for record keeping purposes. The communication unit 44 sends and receives data to and from a server, a system, a client terminal, or the like via a network.

The image managing apparatus 100 comprises a control unit 110, an apparatus information storage 130, an image file generating unit 102, a temporary storage 106, a file processing unit 120, a screen image generating unit 104, and a communication unit 108, and is connected to a recorded image display apparatus 50, and to a controller 140.

The apparatus information storage 130 stores information relating to the image processing apparatus 200. An explanation on a specific example of the image processing apparatus 200 will be given later with reference to FIG. 2. The control unit 110 comprises an apparatus ID acquiring unit 112, an instruction receiving unit 114, an apparatus type acquiring unit 116, and an instruction unit 118.

The apparatus ID acquiring unit 112 acquires an apparatus identifier (ID) for identifying each image processing apparatus 200 from an image processing apparatus 200 when the image managing apparatus 100 is connected with the image processing apparatus 200, when the image managing apparatus 100 is powered on in the state where the image managing apparatus 100 and the image processing apparatus 200 are connected with each other, etc. Then the apparatus ID acquiring unit 112 stores in the apparatus information storage 130 information indicating that the image processing apparatus 200 corresponding to the acquired apparatus identifier is being connected.

The instruction receiving unit 114 receives an instruction from the controller 140, the image processing apparatus 200, or the like. If the instruction receiving unit 114 receives an instruction to capture an image, the apparatus type acquiring unit 116 refers to the apparatus information storage 130 and reads out the type of the image processing apparatus 200 that is being connected.

Based on the type of the image processing apparatus 200 that is being connected, the type having read out by the apparatus type acquiring unit 116, the instruction unit 118 transmits an instruction to the image file generating unit 102, and/or to the file processing unit 120.

In case that the image processing apparatus 200 is of a type that can not transmit an image file directly to the image recording apparatus 40, the image file generating unit 102 receives an instruction from the instruction unit 118, processes a video signal received from the image processing apparatus 200, and generates an image file.

The file processing unit 120 comprises a file acquiring unit 122 and a file transfer unit 124. In case that the image processing apparatus 200 is of a type that can transmit an image file directly to the image recording apparatus 40, the file acquiring unit 122 receives an instruction from the instruction unit 118, and acquires from the image recording apparatus 40 an image file generated by the image processing apparatus 200. In case that the image processing apparatus 200 is of the type that can not transmit an image file directly to the image recording apparatus 40, the file transfer unit 124 receives an instruction from the instruction unit 118, and transfers the image file generated by the image file generating unit 102 to the image recording apparatus 40.

The temporary storage 106 temporarily stores an image file that the image file generating unit 102 in the image managing apparatus 100 has generated, or an image file that the file processing unit 120 acquires from the image recording apparatus 40. The screen image generating unit 104 reads out from the temporary storage 106 the image file that the image file generating unit 102 has generated, or the image file that the file processing unit 120 acquires from the image recording apparatus 40. The screen image generating unit 104 then converts the read image file to a video signal format (e.g. NTSC format, PAL format, etc.) for displaying on a display apparatus so as to generate a screen image to display on the recorded image display apparatus 50.

The communication unit 108 in the image managing apparatus 100 transmits and receives data to and from a server, a system, a client terminal, or the like via a network.

The recorded image display apparatus 50 receives an image that is captured by the endoscope apparatus 220 and recorded in the image recording apparatus 40 from the screen image generating unit 104 in the image managing apparatus 100 and displays the image, accordingly. The controller 140 comprises a pointing device (e.g., a switch, a keyboard, a mouth, a trackball, or the like), a touch panel, a microphone, etc. The controller 140 is used for allowing a user to input an instruction (e.g., an instruction to start capturing an image, to stop capturing an image, to specify a condition for capturing image, to display an image, etc.), and/or for allowing a user to input an interpretation of an image, to input a patient medical record, or the like.

FIG. 2 shows an example of an apparatus information table 300 stored in an apparatus information storage 130. The apparatus information table 300 comprises an apparatus ID field 302, an apparatus type field 304, and an apparatus connection status field 306.

In the apparatus ID field 302, an identifier for identifying each apparatus is written. The apparatus identifier may be an identifier that identifies each image processing apparatus 200 uniquely. Alternatively, the apparatus identifier may be an identifier that identifies the type of image processing apparatus 200, such as a model number or the like. In the apparatus type field 304, the type of image processing apparatus 200 that indicates whether or not the image processing apparatus 200 is of the type that can transmit an image file directly to the image recording apparatus 40 is written for each image processing apparatus 200. In the apparatus connection status field 306, a connection status that indicates whether or not each image processing apparatus 200 is currently connected to the image managing apparatus 100 is written.

In the apparatus information table 300, the apparatus ID field 302 and the apparatus type field 304 are filled in advance for example by reflecting the factory configured state of products.

Alternatively or in addition, the apparatus ID field 302 and the apparatus type field 304 may be configured so as to be updated on-line on as needed basis, for example in case a new image processing apparatus 200 is released, etc. For example, the control unit 110 in the image managing apparatus 100 may acquire information distributed from a manufacturer or the like via a network, and may write information on a new image processing apparatus 200 in the apparatus ID field 302 and in the apparatus type field 304, accordingly. This frees users from the trouble of registering information on an image processing apparatus 200 that is newly released after having purchased an image managing apparatus 100.

Alternatively or in addition, the apparatus ID field 302 and the apparatus type field 304 may be configured so that a user can input information therein. This allows users to freely configure a route for recording an image file by reflecting a network environment, a manner for using an examination apparatuses, etc. of individual medical facilities.

As described above, the apparatus ID acquiring unit 112 acquires the apparatus identifier (ID) of an image processing apparatus 200 from an image processing apparatus 200 when the image managing apparatus 100 and the image processing apparatus 200 are connected with each other, when the image managing apparatus 100 is powered on in the state where the image managing apparatus 100 and the image processing apparatus 200 is connected, etc. The apparatus ID acquiring unit 112 may acquire the apparatus identifier by sending an inquiry to and acquiring a response from the image processing apparatus 200. Alternatively, the apparatus ID acquiring unit 112 may acquire the apparatus identifier by receiving from an image processing apparatus 200 apparatus identifier information transmitted when the image managing apparatus 100 and the image processing apparatus 200 are connected with each other, or at predetermined time intervals.

The apparatus ID acquiring unit 112 changes an apparatus connection status field 306 corresponding to the acquired apparatus identifier to a "being connected" status in the apparatus information table 300 stored in the apparatus information storage 130. If, in the apparatus information table 300, an apparatus connection status field 306 corresponding to an apparatus that can not be detected as being connected indicates a "being connected" status, the apparatus ID acquiring unit 112 changes the apparatus connection status field 306 to a "not connected" status.

If the instruction receiving unit 114 receives an instruction to capture a still image from the image processing apparatus 200, the apparatus type acquiring unit 116 refers to the apparatus information table 300 stored in the apparatus information storage 130 and reads out the type of the image processing apparatus 200 that is being connected with the image managing apparatus 100. More specifically, the apparatus type acquiring unit 116 refers to the apparatus type field 304 of an apparatus of which the apparatus connection status field 306 in the apparatus information table 300 indicates a "being connected" status. Then the apparatus type acquiring unit 116 determines whether or not the connected image processing apparatus 200 is of the type that can transmit an image file directly to the image recording apparatus 40 and allow the image recording apparatus 40 to store the image file.

Figure 3:
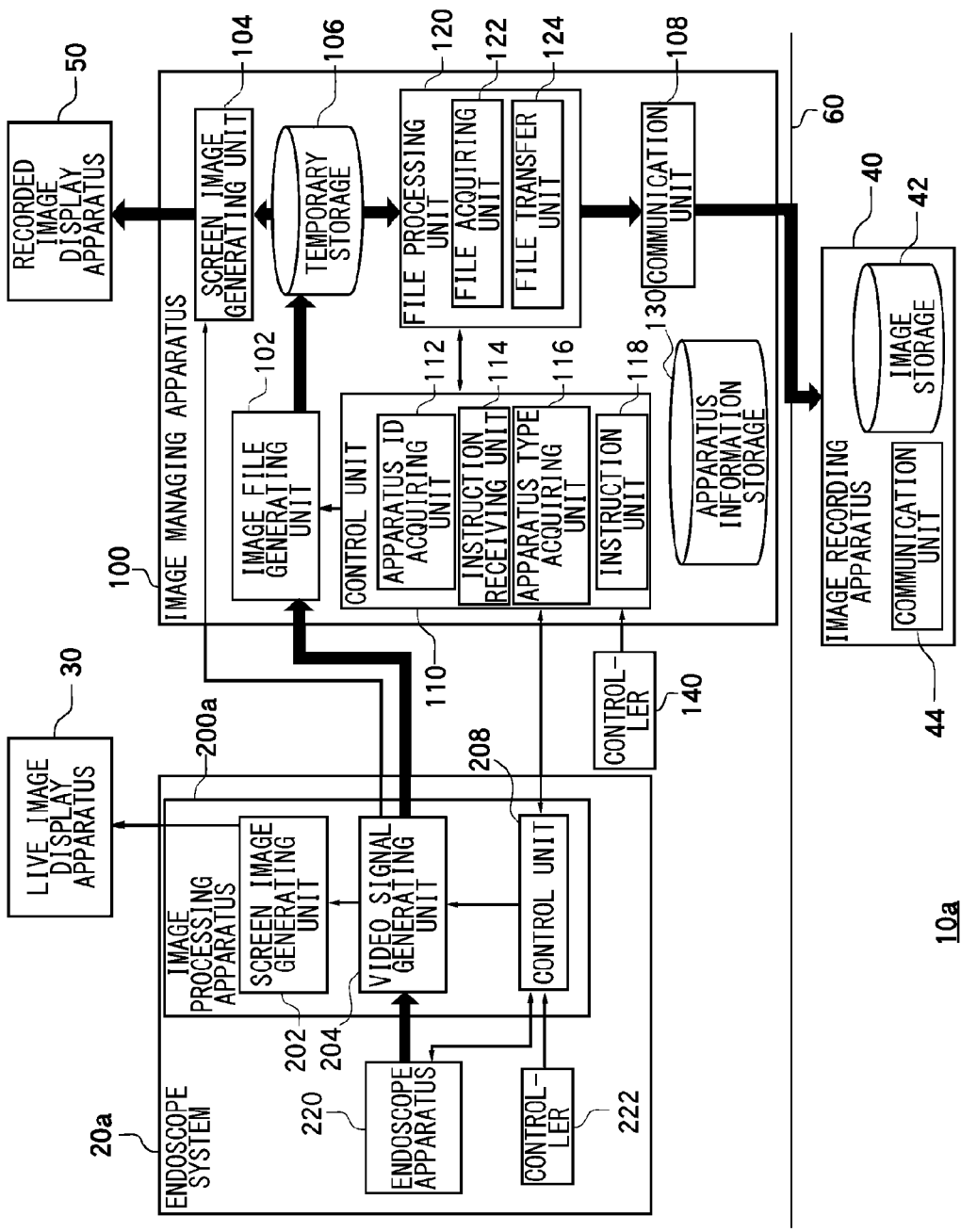
FIG. 3 is a diagram that illustrates a configuration and an operation of the medical examination support system in case that the image managing apparatus according to the exemplary embodiment is connected with an image processing apparatus of a type that can not transmit an image file directly to an image recording apparatus.
Figure 4:
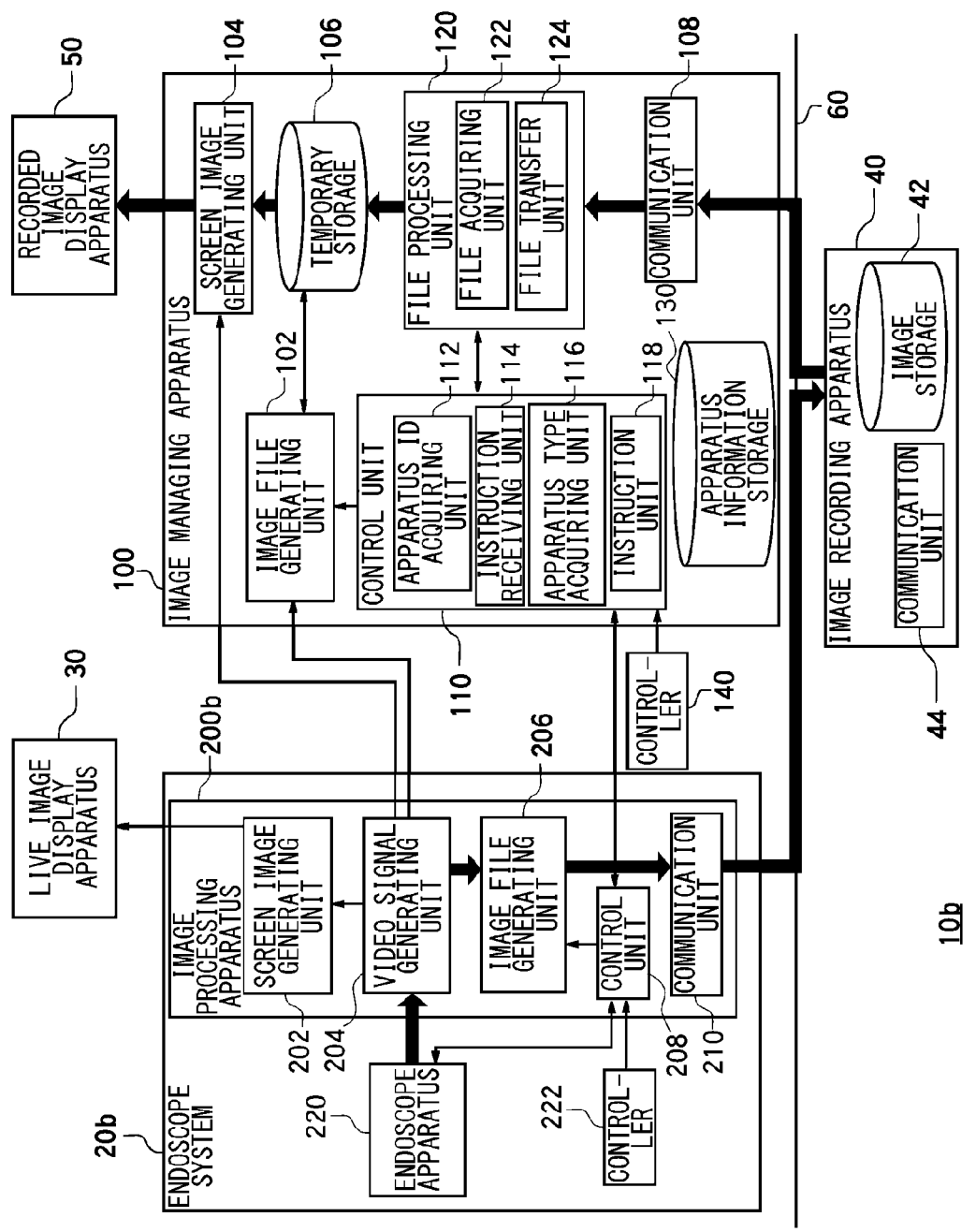
FIG. 4 is a diagram that illustrates a configuration and an operation of the medical examination support system in case that the image managing apparatus according to the exemplary embodiment is connected with an image processing apparatus of a type that can transmit an image file directly to an image recording apparatus.

FIGS. 3 and 4 are diagrams for showing how, in the medical examination support system 10 according to the exemplary embodiment, image files are recorded by using different routes depending on the type of the image processing apparatus 200, and/or depending on the type of image (a still image or a moving image) specified by an instruction to capture an image, and how the recorded image file is displayed on the recorded image display apparatus 50.

FIG. 3 is a diagram for illustrating a configuration of an medical examination support system 10a in case that an image processing apparatus 200a of a type that can not transmit an image file directly to the image recording apparatus 40 is connected with the image managing apparatus 100 according to the exemplary embodiment. The constituting elements on which the same referential number as that of FIG. 1 is attached is configured and operates in a similar manner as the elements shown in FIG. 1, and the explanation thereof is omitted.

The image processing apparatus 200a of the endoscope system 20a includes a video signal generating unit 204, a screen image generating unit 202, and a control unit 208. Upon receiving an instruction from the controller 222 in the endoscope system 20a or from the control unit 110 in the image managing apparatus 100, the control unit 208 outputs a drive control signal for controlling the endoscope apparatus 220, sends the apparatus identifier of the image processing apparatus 200a to the control unit 110 in the image managing apparatus 100, etc.

The video signal generating unit 204 in the image processing apparatus 200a processes the image signal input from the endoscope apparatus 220, performs elimination of noise data, an analog digital conversion, a gain adjustment, an adjustment of luminance ratio, filtering, etc., so as to convert the image signal to a video signal, and outputs the signal to the screen image generating unit 202 in the image processing apparatus 200a, and to the image managing apparatus 100. The screen image generating unit 202 in the image processing apparatus 200a converts the image signal input from the video signal generating unit 204 to a video signal format (e.g. NTSC format, PAL format, etc.) for displaying on a display apparatus, so as to generate a screen image for displaying on the live image display apparatus 30, and outputs to the live image display apparatus 30, accordingly.

If the instruction receiving unit 114 receives an instruction to capture a still image from the image processing apparatus 200a, the apparatus type acquiring unit 116 in the image managing apparatus 100 refers to the apparatus information table 300 stored in the apparatus information storage 130 and reads out the type of the image processing apparatus 200a that is being connected with the image managing apparatus 100, as described above with reference to FIGS. 1 and 2. In case of the configuration shown in FIG. 3, the apparatus type acquiring unit 116 determines that the connected image processing apparatus 200a is of the type that cannot transmit an image file directly to the image recording apparatus 40 and cannot allow the image recording apparatus 40 to store the image file, and transmits the result of the determination to the instruction unit 118.

In this case, the instruction unit 118 sends an instruction to generate an image file to the image file generating unit 102 in the image managing apparatus 100. The image file generating unit 102 processes the video signal received from the image processing apparatus 200, and generates an image file. Although the image file may be generated in JPEG format, GIF format, TIFF format, or the like, the format of the image file is not limited to these but any file format that has a file size transmittable via a network, and storable in the image storage 42 can be adopted. The image file generating unit 102 stores the generated image file in the temporary storage 106.

The file transfer unit 124 transfers the image file that is generated by the image file generating unit 102 and stored in the temporary storage 106 to the image recording apparatus 40 so that the image file is stored in the image storage 42 in the image recording apparatus 40.

The screen image generating unit 104 in the image managing apparatus 100 converts the image file that the image file generating unit 102 in the image managing apparatus 100 generates and stores in the temporary storage 106 to a video signal format for displaying on the recorded image display apparatus 50, generates a screen image, and outputs the screen image to the recorded image display apparatus 50, accordingly. Thereby an image file of which an image is captured by the endoscope apparatus 220 and which is generated by the image managing apparatus 100 can be stored in the image storage 42 in the image recording apparatus 40, and can be displayed on the recorded image display apparatus 50.

On the other hand, in case the instruction receiving unit 114 receives an instruction to capture a moving image, the apparatus type acquiring unit 116 in the image managing apparatus 100 does not read out the type of the connected image processing apparatus 200a, but sends an instruction to generate an image file to the image file generating unit 102 in the image managing apparatus 100. Thereafter, a moving image file is generated, stored, and displayed in a similar manner as that of the explanation given above for a still image.

More specifically, the image file generating unit 102 processes a video signal transmitted from the image processing apparatus 200, generates a moving image file, and stores the file in the temporary storage 106. The file transfer unit 124 transfers the moving image file that is generated by the image file generating unit 102 and stored in the temporary storage 106 to the image recording apparatus 40 in order to store the moving image file in the image storage 42 in the image recording apparatus 40. The screen image generating unit 104 in the image managing apparatus 100 converts the moving image file that the image file generating unit 102 in the image managing apparatus 100 generates and stores in the temporary storage 106 to a video signal format in order to display on the recorded image display apparatus 50, so as to generate a screen image, and outputs the screen image to the recorded image display apparatus 50, accordingly.

This allows the image managing apparatus 100 to generate an image file and allows the image file generated by the image managing apparatus 100 to be stored in the image storage 42 in the image recording apparatus 40 every time regardless of the type of the image processing apparatus 200 in case of recording a moving image. Further, an image generated by the image managing apparatus 100 can be displayed on the recorded image display apparatus 50. In this manner, by regularly using a same route in order to transfer an image file in case of a moving image, which typically has a large file size, a network can be effectively configured in advance while taking network loads into consideration. Thus, a situation where transmission of a moving image causes a network congestion can be avoided.

FIG. 4 is a diagram for illustrating a configuration of an medical examination support system 10b in case that an image processing apparatus 200b of a type that can transmit an image file directly to the image recording apparatus 40 is connected with the image managing apparatus 100 according to the exemplary embodiment. The constituting elements on which the same referential number as that of FIG. 1 or FIG. 3 is attached is configured and operates in a similar manner as the elements shown in FIG. 1 or FIG. 3, and the explanation thereof is omitted.

The image processing apparatus 200b in the endoscope system 20b further comprises an image file generating unit 206 and a communication unit 210 in addition to the constituting elements shown in FIG. 3.

The image file generating unit 206 in the image processing apparatus 200b processes a video signal transmitted from the video signal generating unit 204 and generates an image file. Accordingly, the control unit 208 of the image processing apparatus 200 transfers the image file that is generated by the image file generating unit 206 to the image storage 42 via the communication unit 210 of the image processing apparatus 200b, via the network 60, and via the communication unit 44 of the image recording apparatus 40 so that the image file is stored in the image storage 42 in the image recording apparatus 40.

If the instruction receiving unit 114 receives an instruction to capture a still image from the image processing apparatus 200b, the apparatus type acquiring unit 116 in the image managing apparatus 100 refers to the apparatus information table 300 in the apparatus information storage 130 and reads out the type of the connected image processing apparatus 200, following a procedure described above with reference to FIGS. 1 and 2. In case of the configuration shown in FIG. 4, the apparatus type acquiring unit 116 determines that the connected image processing apparatus 200b is of the type that can transmit an image file directly to the image recording apparatus 40 and allow the image recording apparatus 40 to store the image file, and transmits the result of the determination to the instruction unit 118.

The instruction unit 118 sends an instruction not to generate an image file to the image file generating unit 102 in the image managing apparatus 100. The image file generating unit 102 in the image managing apparatus 100 does not generate an image file even if the image file generating unit 102 receives a video signal from the video signal generating unit 204 in the image processing apparatus 200b. The instruction unit 118 sends an instruction to acquire an image file to the file acquiring unit 122. The file acquiring unit 122 reads an image file, which is sent directly from the image processing apparatus 200b to the image recording apparatus 40, from the image storage 42 in the image recording apparatus 40.

First, the file acquiring unit 122 checks whether or not an image file generated by the image processing apparatus 200b is stored in the image storage 42. More specifically, the file acquiring unit 122 searches the image storage 42 in the image recording apparatus 40, sends an inquiry to and receives an response from the image recording apparatus 40, receives information on file generation sent from the image recording apparatus 40, etc. Accordingly, the file acquiring unit 122 determines whether or not an image file generated by the image processing apparatus 200 is stored in the image storage 42 in the image recording apparatus 40, and in case that an image file generated by the image processing apparatus 200 is stored in the image storage 42, acquires the image file, and stores the image file in the temporary storage 106.

The screen image generating unit 104 in the image managing apparatus 100 converts the image file that the file acquiring unit 122 acquires and stores in the temporary storage 106 to a video signal format for displaying on the recorded image display apparatus 50, so as to generate a screen image, and outputs the screen image to the recorded image display apparatus 50, accordingly. Thereby an image captured by the endoscope apparatus 220 and stored in the image recording apparatus 40 can be displayed on the recorded image display apparatus 50. Further, in case that the image processing apparatus 200 is of the type that can generate an image file and can transmit the image file directly to an image recording apparatus, the system can avoid waste or confusion resulting from redundancy that both of the image processing apparatus 200b and the image managing apparatus 100 respectively generate an image file and store the image file in an recording apparatus.

On the other hand, in case the instruction receiving unit 114 receives an instruction to capture a moving image from the image processing apparatus 200b, the apparatus type acquiring unit 116 in the image managing apparatus 100 does not read out the type of a connected apparatus, but sends an instruction to generate an image file to the image file generating unit 102 in the image managing apparatus 100. Thereafter, the image managing apparatus 100 generates an image file, the generated image file is stored in the image recording apparatus 40, and a screen image for displaying on the recorded image display apparatus 50 is generated in a similar manner as described above with reference to FIG. 3.

This allows the image managing apparatus 100 to generate an image file and allows the image file generated by the image managing apparatus 100 to be stored in the image recording apparatus 40 every time regardless of the type of the image processing apparatus 200 in case of recording a moving image. Further, an image generated by the image managing apparatus 100 can be displayed on the recorded image display apparatus 50. In this manner, by regularly using a same route in order to transfer an image file in case of a moving image, which typically has a large file size, a network can be effectively configured in advance while taking network loads into consideration. Therefore, a situation where transmission of a moving image causes a network congestion can be avoided.

In the configurations shown in FIGS. 1, 3, and 4, the video signal transmitted from the video signal generating unit 204 in the image processing apparatus 200 may be directly input to the screen image generating unit 104 in the image managing apparatus 100 and may be displayed on the recorded image display apparatus 50. Thereby, an image captured by an endoscope camera during an examination can be displayed as a live image also on the recorded image display apparatus 50, in case that no instruction to record a captured image is issued.

Figure 5:
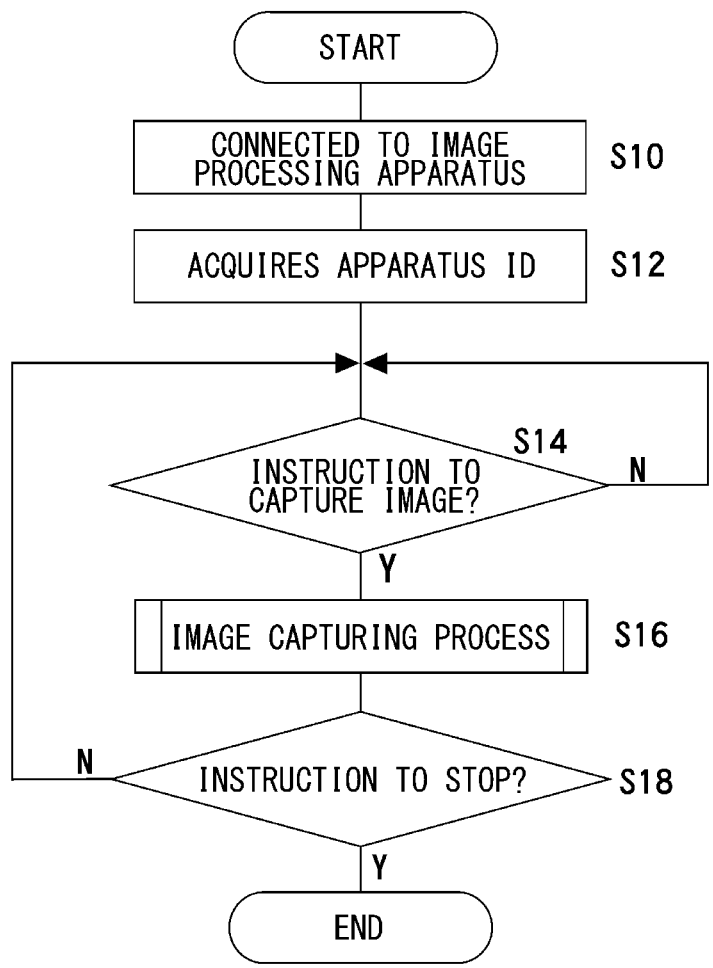
FIG. 5 shows a flowchart indicating a processing procedure in the image managing apparatus to record an image captured by an endoscope apparatus and to allow a recorded image display apparatus to display the image.

An explanation on the operation with the aforementioned configuration will be given below. FIG. 5 shows a flowchart indicating a processing procedure for the image managing apparatus 100 to store an image captured by the endoscope apparatus 220 in the image storage 42 and to allow the recorded image display apparatus 50 to display the image in case of an examination using the endoscope apparatus 220.

First, a user connects the image processing apparatus 200 and the image managing apparatus 100 with each other by a cable or the like, or switches on the power of the image managing apparatus 100 in the state where the image managing apparatus 100 and the image processing apparatus 200 are connected with each other (S10). Then the apparatus ID acquiring unit 112 in the image managing apparatus 100 acquires the apparatus identifier of the image processing apparatus 200 (S12), and stores the identifier in the apparatus information storage 130 as information on a connected apparatus.

Thereafter, until receiving an instruction to capture an image (N in S14), the image managing apparatus 100 does not perform an image capturing process and stands by. If the user inputs an instruction to capture a still image or a moving image through the controller 222 in the endoscope system 20 or through the controller 140 in the image managing apparatus 100, the instruction receiving unit 114 in the image managing apparatus 100 receives the instruction (Y in S14), and performs an image capturing process (S16). Until receiving an instruction to stop capturing an image (N in S18), the image capturing process is performed (S16) every time an instruction to capture an image is received. If the instruction receiving unit 114 in the image managing apparatus 100 receives an instruction to stop capturing an image (Y in S18), the examination is completed.

Figure 6:
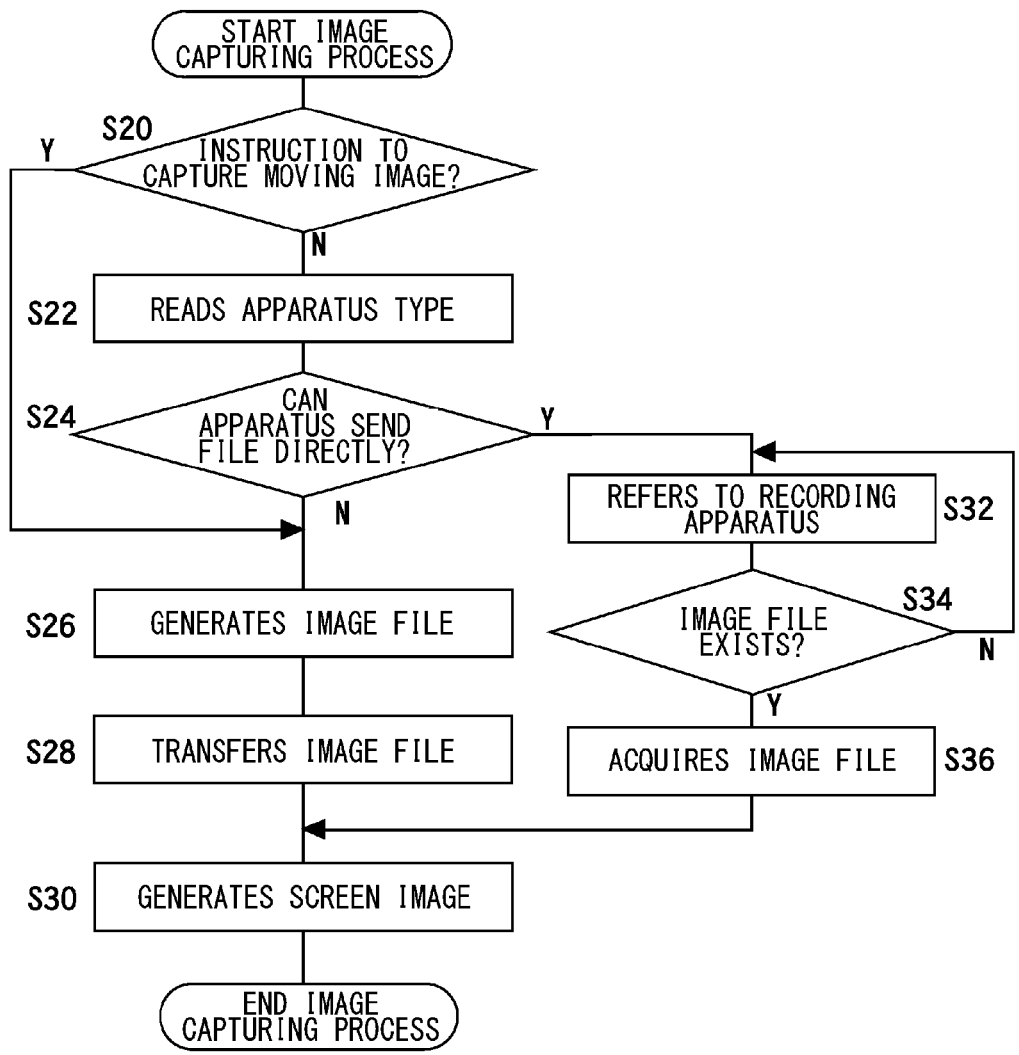
FIG. 6 shows a flowchart indicating a procedure of the image capturing process in the flowchart in FIG. 5.

FIG. 6 shows a flowchart indicating a procedure of the image capturing process in the flowchart in FIG. 5. If an instruction received by the instruction receiving unit 114 is an instruction to capture a still image (N in S20), the apparatus type acquiring unit 116 reads out the type of the connected image processing apparatus 200 from the apparatus information storage 130, and based on the read apparatus identifier, the apparatus type acquiring unit 116 reads out the type of the connected image processing apparatus 200 (S22).

In case that the connected image processing apparatus 200 is determined to be of the type that can not transmit an image file directly to the image recording apparatus 40 (N in S24), the image file generating unit 102 processes a video signal transmitted from the image processing apparatus 200 and generates an image file (S26), and stores the file in the temporary storage 106, accordingly. The file transfer unit 124 transfers the still image file that is generated by the image file generating unit 102 and is stored in the temporary storage 106 to the image recording apparatus 40 so that the image file is stored in the image storage 42 in the image recording apparatus 40 (S28). The screen image generating unit 104 in the image managing apparatus 100 generates a screen image for displaying the image file that the image file generating unit 102 generates and stores in the temporary storage 106 (S30) and outputs the screen image to the recorded image display apparatus 50.

Although in the flow chart, the process of generating a screen image to be displayed of step S30 is performed after the process of transferring an image file of step S28, those steps may be performed in parallel in the actual implementation. Alternatively, the process of generating a screen image to be displayed of step S30 may be performed before the process of transferring an image file of step S28.

By contrast, in case that the connected image processing apparatus 200 is of the type that can transmit an image file directly to the image recording apparatus 40 (Y in S24), the image file generating unit 102 does not generate an image file from the video signal transmitted from the image processing apparatus 200.

In this case, the file acquiring unit 122 refers to the image storage 42 and checks whether or not the image processing apparatus 200 has created an image file and stored the file in the image storage 42 (S32). If a generated image file is not stored in the image storage 42 (N in S34), the file acquiring unit 122 stands by. If a generated image file is already stored (Y in S34), the file acquiring unit 122 acquires the image file that the image processing apparatus 200 created and stored in the image storage 42 (S36). The screen image generating unit 104 in the image managing apparatus 100 generates a screen image for displaying the image file generated by the image processing apparatus 200 (S30) and allows the recorded image display apparatus 50 to display the screen image.

On the other hand, if the instruction received by the instruction receiving unit 114 is an instruction to capture a moving image (Y in S20), the image file generating unit 102 processes a video signal transmitted from the image processing apparatus 200 and generates a moving image file (S26), and stores the file in the temporary storage 106, regardless of the type of the connected image processing apparatus 200. The file transfer unit 124 transfers the moving image file that the image file generating unit 102 generated and stored in the temporary storage 106 to the image storage 42 in the image recording apparatus 40 (S28). The screen image generating unit 104 in the image managing apparatus 100 generates a screen image for displaying the moving image file generated by the image file generating unit 102 (S30) and allows the recorded image display apparatus 50 to display the screen image.

Therefore, a user can effectively record a medical examination image even without knowing the difference between image processing apparatuses in terms of a model number or the like.

A description on a variation of the exemplary embodiment will be given below. According to the variation of exemplary embodiment, if the communication unit 108 in the image managing apparatus 100 detects that the image processing apparatus 200 is not connected with the network 60, the image managing apparatus 100 generates an image file, regardless of the type of the image processing apparatus 200 and regardless of whether an instruction to capture an image is on a moving image or is about a still image.

An image managing apparatus 100 according to the variation of the embodiment is configured and operates in a similar manner as the image managing apparatus 100 in FIGS. 1, 3 and 4, and an explanation will mainly be given of differences from the exemplary embodiment described above. In the image managing apparatus 100 according to the variation of exemplary embodiment, if the communication unit 108 in the image managing apparatus 100 detects that the image processing apparatus 200, which is being connected with the image managing apparatus 100, is not connected with the network 60, the instruction unit 118 writes that the apparatus 200 can not be connected to a network in a network status field (not shown) corresponding to the image processing apparatus 200 of which the connection status is "being connected" in the apparatus information table 300 stored in the apparatus information storage 130.

If the instruction receiving unit 114 receives an instruction to capture an image from the image processing apparatus 200, the apparatus type acquiring unit 116 refers to the network status field of the connected apparatus. If the network status indicates that the apparatus cannot be connected to a network, the apparatus type acquiring unit 116 does not read out the type of the apparatus. Then the instruction unit 118 sends an instruction to generate an image file to the image file generating unit 102 in the image managing apparatus 100.

Thereafter, processes are carried out in a similar manner as described above with reference to FIG. 3. That is, the image file generating unit 102 processes a video signal transmitted from the image processing apparatus 200, generates an image file, and stores the file in the temporary storage 106. The instruction unit 118 issues an instruction to the file transfer unit 124 to transfer the file. The file transfer unit 124 transfers the image file that the image file generating unit 102 generated and stored in the temporary storage 106 to the image recording apparatus 40 so that the image file is stored in the image storage 42 in the image recording apparatus 40. The screen image generating unit 104 in the image managing apparatus 100 converts the image file stored in the temporary storage 106 to a video signal format for displaying on the recorded image display apparatus 50, so as to generate a screen image, and outputs the screen image to the recorded image display apparatus 50, accordingly.

This allows the image managing apparatus 100 to generate an image file and to send the image file to the image recording apparatus 40 every time regardless of the type of the image processing apparatus 200 and regardless of whether an instruction to capture an image is on a moving image or on a still image, in case of the image processing apparatus 200 is obviously not connected to the network 60.

A description on another variation of the exemplary embodiment will be given below. An image managing apparatus 100 according to the variation of the embodiment is also configured and operates in a similar manner as the image managing apparatus 100 in FIGS. 1, 3 and 4, and an explanation will mainly be given of differences from the exemplary embodiment described above. According to the variation, the image file generating unit 102 in the image managing apparatus 100 generates an image file and stores the image file in the temporary storage 106 every time regardless of the type of the image processing apparatus 200, and if the image file is not necessary, the image file is discarded later.

The instruction receiving unit 114 receives an image capturing instruction (e.g., an instruction to start capturing an image, an instruction to stop capturing an image, or the like) from the image processing apparatus 200. According to the variation, information on the time when an instruction is issued is attached to the instruction. In addition, image capturing time information is attached also to an image file generated by the image managing apparatus 100 or by the image processing apparatus 200.

According to the variation, an image file is tentatively generated in the image managing apparatus 100, even if the image processing apparatus 200 that is connected with the image managing apparatus 100 is of the type that can transmit an image file directly to the image recording apparatus 40 so as to record the image file (as in the case of the image processing apparatus 200b shown in FIG. 4). More specifically, in case the instruction receiving unit 114 receives an instruction to capture an image, the instruction unit 118 sends an instruction to generate an image file to the image file generating unit 102 in the image managing apparatus 100, every time regardless of the type of the image processing apparatus 200. The image file generating unit 102 processes a video signal received from the image processing apparatus 200, generates an image file, and stores the file in the temporary storage 106.

In case that the image processing apparatus 200 connected with the image managing apparatus 100 is of the type that can transmit an image file directly to the image recording apparatus 40 and stores the file, the instruction unit 118 sends an image file acquisition instruction, which is an instruction to acquire from the image recording apparatus 40 an image file created by the image processing apparatus 200b, to the file acquiring unit 122, as described above with reference to FIG. 4. According to the variation of the embodiment, the instruction unit 118 sends to the file acquiring unit 122 an instruction to discard an image file that the image file generating unit 102 generated and stored in the temporary storage 106 if the file acquiring unit 122 can acquire an image file.

If an image file generated by the image processing apparatus 200b is stored in the image storage 42 in the image recording apparatus 40, the file acquiring unit 122 acquires the image file, and stores the image file in the temporary storage 106. In this process, if image files stored in the temporary storage 106 includes an image file with a same image capturing time as that of the image file acquired by the file acquiring unit 122, the file acquiring unit 122 discards the image file stored in the temporary storage 106.

On the other hand, if the file acquiring unit 122 can not acquire an image file stored in the image storage 42 in the image recording apparatus 40 by the time when a predetermined file acquiring reference time elapses after the file acquiring unit 122 receives the instruction to acquire an image file, the file acquiring unit 122 does not delete an image file in the temporary storage 106. The file acquiring unit 122 reports that the unit 122 could not acquire an image file to the instruction unit 118, accordingly. Upon receiving the report, which indicates that an image file could not be acquired, from the file acquiring unit 122, the instruction unit 118 issues an instruction to the file transfer unit 124 to transfer a file. Upon receiving the instruction to transfer a file, the file transfer unit 124 transfers the image file that the image file generating unit 102 generated and stored in the temporary storage 106 to the image recording apparatus 40 so that the image file is stored in the image storage 42 in the image recording apparatus 40.

The predetermined file acquiring reference time refers to a time period that serves as a threshold value for determining whether or not to take another measure in case a file cannot be acquired, in accordance with a time elapsed while the file acquiring unit 122 can not acquire a file. The predetermined file acquiring reference time is determined by, for example, adding an admissible delay time to an averaged time required for the medical examination support system 10 to store a captured image file in the image storage 42 after an instruction to capture an image is issued and the control unit 208 in the image processing apparatus 200 receives the instruction to capture an image. The predetermined file acquiring reference time may be determined by experiment or based on experience. Alternatively, the predetermined file acquiring reference time may be configured so that a user can define the reference time by taking situations in respective medical facilities into account.

The screen image generating unit 104 in the image managing apparatus 100 converts an image file stored in the temporary storage 106 to a video signal format for displaying on the recorded image display apparatus 50, so as to generate a screen image, and outputs the screen image to the recorded image display apparatus 50, accordingly.

According to the variation, an image file that the image managing apparatus 100 has generated and stored temporarily can be used as a file for record, even in case that due to the occurrence of some trouble the image processing apparatus 200 can not generate an image file or in case a generated image file can not be stored in the image storage 42. Therefore, an image managing apparatus with higher reliability can be provided. Further, a situation can be avoided where the examination time is prolonged so as to capture another image, or re-examination is performed due to a recording failure.

Given above is an explanation based on the exemplary embodiments. The exemplary embodiments described above are intended to be illustrative only and various combinations of elements of the exemplary embodiments are also within the scope of the present invention. An exemplary embodiment obtained by combining the described exemplary embodiments has an advantage that is a combination of respective advantages of constituent exemplary embodiments. Various modifications could be developed based on the knowledge of those skilled in the art and such modifications are also within the scope of the present invention.

An explanation has been given on an example of an image captured by an endoscopic examination apparatus according to the exemplary embodiments. However, the scope of the present invention is not limited to this example. The present invention can be applied to a case where both of: a) an apparatus that can generate an image file for storing electronically in a recording apparatus and can transmit the image file directly to the recording apparatus; and b) an apparatus that can not generate and can not transmit an image file directly to the recording apparatus are used. For example, the present invention can be applied to management of medical image data (e.g., X-ray data, CT scan data, MRI data, ultrasound data, or the like) or wave data such as electrocardiogram data, or the like.

As described above, the present invention can be used for an image managing apparatus for processing images captured by a medical examination device.

What is claimed is:

1. An image managing apparatus configured to be connected to an image processing apparatus that receives an image signal from an imaging apparatus which captures a medical examination image, and to be connected to an image recording apparatus that records a captured image, comprising an apparatus information storage operative to store an image processing apparatus identifier and an image processing apparatus type, which indicates whether or not the image processing apparatus can transmit an image file directly to the image recording apparatus, while associating the identifier and the type with each other for more than one image processing apparatuses;

an apparatus ID acquiring unit operative to acquire an image processing apparatus identifier from the connected image processing apparatus;

an apparatus type acquiring unit operative to refer to the apparatus information storage on the basis of the image processing apparatus identifier acquired by the apparatus ID acquiring unit and operative to read out the type of the connected image processing apparatus;

an image file acquiring unit operative, if the image processing apparatus type read by the apparatus type acquiring unit indicates that the image processing apparatus can transmit an image file directly to the image recording apparatus, to read out from the image recording apparatus an image file that the image processing apparatus stores directly in the image recording apparatus;

an image file generating unit operative, if the image processing apparatus type read by the apparatus type acquiring unit indicates that the image processing apparatus can not transmit an image file directly to the image recording apparatus, to process a video signal transmitted from the image processing apparatus and to generate an image file;

an image file transfer unit operative to transfer the image file generated by the image file generating unit to the image recording apparatus in order to allow the image recording apparatus to store the image file; and a screen image generating unit operative to generate a screen image for displaying the image file generated by the image file generating unit or the image file acquired by the image file acquiring unit on a display.

2. The image managing apparatus according to claim 1 further comprising an instruction receiving unit operative to receive an instruction to capture an image, wherein in case that the instruction receiving unit receives an instruction to capture a still image, the apparatus type acquiring unit refers to the apparatus information storage and reads out the type of the connected image processing apparatus, and in case that the image processing apparatus type read by the apparatus type acquiring unit indicates that the image processing apparatus can transmit an image file directly to the image recording apparatus, the image file generating unit does not generate an image file from the video signal transmitted from the image processing apparatus.

3. The image managing apparatus according to claim 2, wherein if the instruction receiving unit receives an instruction to capture a moving image:

the image file generating unit processes the video signal transmitted from the image processing apparatus and generates an image file; and the image file transfer unit transfers the image file generated by the image file generating unit to the image recording apparatus in order to allow the image recording apparatus to store the image file.

4. The image managing apparatus according to claim 1 further comprising an instruction receiving unit operative to receive an instruction to capture an image, wherein in case that the image processing apparatus type read by the apparatus type acquiring unit indicates that the image processing apparatus can transmit an image file directly to the image recording apparatus:

the image file generating unit generates an image file from the video signal transmitted from the image processing apparatus; and if the image file acquiring unit can not acquire the image file generated by the image processing apparatus from the image recording apparatus by the time when a predetermined file acquiring reference time elapses after the instruction receiving unit receives from the image processing apparatus an instruction to acquire an image file, the image file acquiring unit does not delete the image file generated by the image file generating unit, and the image file transfer unit transfers the image file generated by the image file generating unit to the image recording apparatus in order to allow the image recording apparatus to store the image file.

5. The image managing apparatus according to claim 1 further comprising a communication unit operative to communicate via a network, wherein if the communication unit detects that the image processing apparatus is not connected to the network, the image file generating unit processes the video signal transmitted from the image processing apparatus and generates an image file; and the image file transfer unit transfers the generated image file to the image recording apparatus in order to allow the image recording apparatus to store the image file.

6. The image managing apparatus according to claim 1, wherein the imaging apparatus is an endoscope apparatus.

7. A method for controlling an image managing system that manages a medical examination image, comprising:

storing, by an apparatus information storage, an image processing apparatus identifier and an image processing apparatus type, which indicates whether or not the image processing apparatus can transmit an image file directly to an image recording apparatus, while associating the identifier and the type with each other for more than one image processing apparatuses for processing an image signal received from an imaging apparatus;

acquiring, by an apparatus ID acquiring unit, an image processing apparatus identifier from an image processing apparatus to be controlled;

referring, by an apparatus type acquiring unit, to the apparatus information storage on the basis of the image processing apparatus identifier acquired by the apparatus ID acquiring unit and reading the type of the image processing apparatus;

if the image processing apparatus type read by the apparatus type acquiring unit indicates that the image processing apparatus can transmit an image file directly to the image recording apparatus, reading, by an image file acquiring unit, from the image recording apparatus an image file that the image processing apparatus stores directly in the image recording apparatus;

if the image processing apparatus type read by the apparatus type acquiring unit indicates that the image processing apparatus can not transmit an image file directly to the image recording apparatus, processing, by an image file generating unit, a video signal transmitted from the image processing apparatus and generating an image file;

transferring, by an image file transfer unit, the image file generated by the image file generating unit to the image recording apparatus in order to allow the image recording apparatus to store the image file; and generating, by a screen image generating unit, a screen image for displaying the image file generated by the image file generating unit or the image file acquired by the image file acquiring unit on a display.

* * * * *